United States Patent [19]

Thaer et al.

[11] 4,363,536

[45] Dec. 14, 1982

[54] INSTRUMENT BASE FOR OPTICAL DEVICES

[75] Inventors: Andreas Thaer, Leigestern; Willi Hagner, Solms; Horst Frimmel, Hermannstein; Horst Riegel, Wetzlar-Bueblingshausen, all of Fed. Rep. of Germany

[73] Assignee: Ernst Leitz Wetzlar GmbH, Wetzlar, Fed. Rep. of Germany

[21] Appl. No.: 172,229

[22] Filed: Jul. 25, 1980

[30] Foreign Application Priority Data

Jul. 27, 1979 [DE] Fed. Rep. of Germany ... 7921541[U]

[51] Int. Cl.³ .............................................. A61B 3/00
[52] U.S. Cl. ................................................... 351/245
[58] Field of Search .......................... 351/7, 16, 38, 39

[56] References Cited

U.S. PATENT DOCUMENTS 4,187,005 2/1980 Rosenberger .......................... 351/38

Primary Examiner—John K. Corbin
Assistant Examiner—Rodney Bovernick
Attorney, Agent, or Firm—Schwartz, Jeffery, Schwaab, Mack, Blumenthal & Koch

[57] ABSTRACT

Disclosed is an adjustable instrument base suitable for holding optical instruments, comprising a base plate movable along first and second horizontal coordinate directions; a housing member surrounding the base plate and being movable with respect to the base plate in the first coordinate direction; first and second mechanisms mounted on the housing member for effecting displacement of the base plate in the first and second coordinate directions, respectively; a generally U-shaped stirrup member mounted on the base plate for rotation; a support plate mounted on the stirrup member for rotation about a horizontal axis; a first and preferably second instrument carriers displaceably mounted on the support plate; and a mechanism mounted on said base plate for effecting vertical displacement of the first instrument carrier.

12 Claims, 3 Drawing Figures

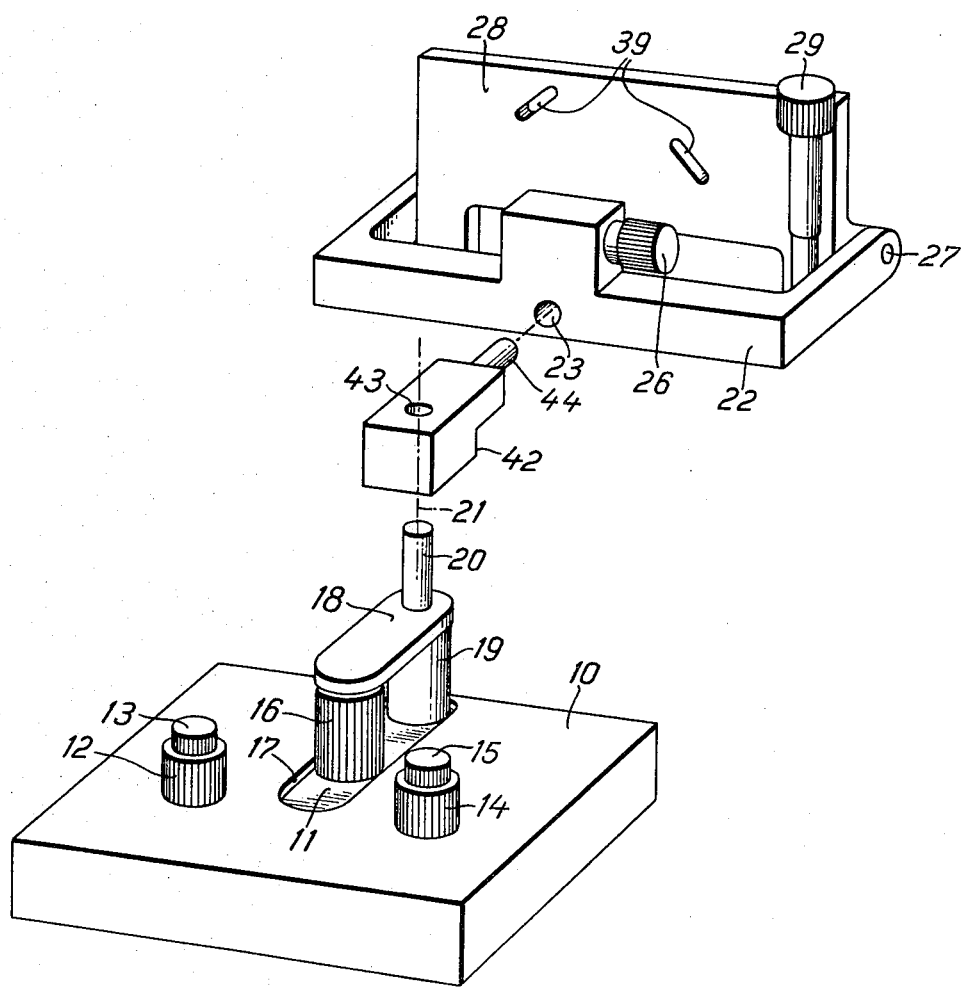

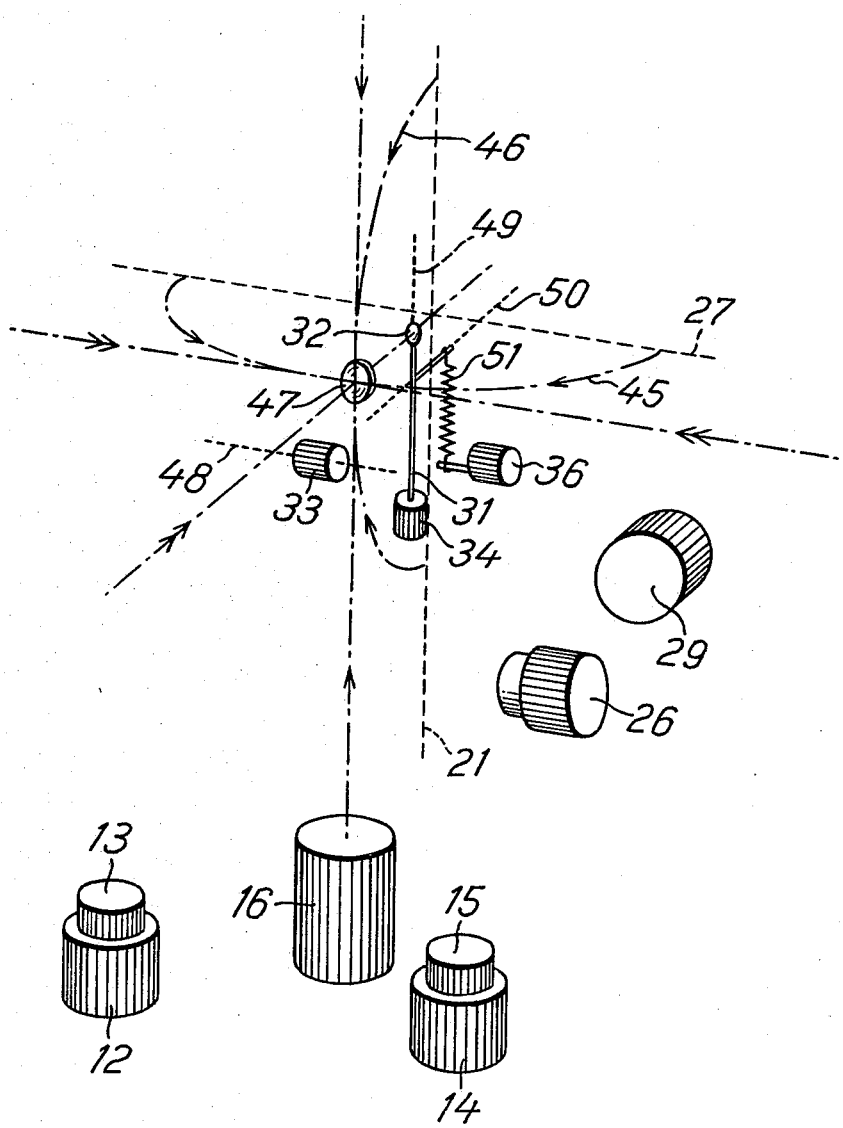

INSTRUMENT BASE FOR OPTICAL DEVICES

BACKGROUND OF THE INVENTION

The present invention relates to an instrument base for optical devices, such as ophthalmological or intravital microscopic instruments, and more particularly to such an instrument base having a horizontally displaceable base plate and a horizontally rotatable instrument carrier, which is adjustable in height and is arranged above the base plate.

Instrument bases for optical devices and, in particular, for ophthalmological examining instruments are known in different design forms. The construction of such instrument bases is determined essentially by the size and the weight of the structural parts to be mounted on them and by the precision and versatility of possible settings. The accurate optical and geometrical adjustability of the instrument to the object to be examined is an absolute requirement. This is particularly true when optical structural elements are to be placed in direct contact with the organ to be examined.

A typical example for an arrangement of this type is an instrument for the examination of frontal sections of the eye, such as for example the epithelium or endothelium of the cornea at higher magnifications. In the process, in order to achieve optical results, it is often impossible to avoid a direct contact of the eye to be examined with an objective lens or an adapter lens which is separate from the objective lens.

In addition to coarse focusing and the feasibility of quickly changing positions on the eye to be examined, in this case there should also be possible a subsequent fine focusing and fine adjustment in the direction of the X-Y coordinates, as well as an adjustability of the contact lens in the horizontal and vertical directions independently of the overall settings of the instrument base.

In DL-P No. 60,443 is disclosed a device for the fine adjustment of ophthalmological instruments, having a lever rotatable in all directions in the horizontal plane for setting purposes, and a spindle equipped with threads and engaging a hub for adjustments in height. The lever is rotatable about its longitudinal axis and is connected both with the lever and with the hub. In this manner, the lever may be used both for horizontal and vertical adjustment. Examinations with stronger magnification in the micro range, as is frequently required, for example, in relation to the epithelium or endothelium of the cornea and direct contact with the eye being examined are not feasible with this arrangement.

The same is true for the arrangement known from DE-AS No. 1,189,759 which includes an illumination and observation device rotatable around a vertical axis, whereby the latter is also rotatable around an axis which passes through the eye to be examined and which stands perpendicular to the direction of the observation. In this manner, details particularly in the upper and lower parts of the frontal regions of the eye may be observed well, but because of the variable height and inclination of the viewing direction, the arrangement is inconvenient.

DE-OS No. 2,520,445 discloses an arrangement for the examination of the eye having a microscope mounted on a support arm, wherein the support arm may be rotated around a swivel axis. A thumb lever, a knurled knob and a rotatable finger are provided for adjustment. Direct contacting is again not possible with this device. Furthermore, the device is not suitable for use with micro objectives having strong inherent magnification or for distortion-free image reproduction in photographic recording, because of its low stability.

Other known devices provide rapid adjustments in the horizontal and vertical planes with adequate accuracy but are not designed for either horizontal or vertical rotation or cannot be readjusted from vertical to oblique observation. Particularly in the examination of the endothelial cell structure at the rear side of the cornea, such an adjustment is especially advantageous by making possible observations at the angle of reflection of the light incident on the object plane.

SUMMARY OF THE INVENTION

It is therefore an object of the present invention to provide an improved instrument base.

It is also an object of the invention to provide a stable instrument base which is adjustable rapidly, precisely and in a functionally correct manner in the horizontal and vertical planes.

A further object of the invention resides in providing an instrument base which makes it possible to examine a wide area of the object, even in the micro range, while maintaining direct contact of an optical contact element with the surface of the object.

Still another object of the invention resides in the provision of an instrument base which is readily readjusted to perform oblique observations.

It is also an object of the invention to provide an instrument which includes the improved base according to the invention.

In accomplishing the foregoing objects, there has been provided in accordance with the present invention an adjustable instrument base suitable for holding optical instruments, comprising a base plate movable along first and second horizontal coordinate directions; a housing member surrounding the base plate and being movable with respect to the base plate in the first coordinate direction; first and second means mounted on the housing member for effecting displacement of the base plate in the first and second coordinate directions, respectively; a generally U-shaped stirrup member mounted on the base plate for rotation, preferably about a vertical axis; a support plate mounted on the stirrup member for rotation about a horizontal axis; a first instrument carrier displaceably mounted on the support plate; and means mounted on the base plate for effecting vertical displacement of the first instrument carrier. Preferably, the instrument base further comprises a second carrier for an optical contact element displaceably mounted on the support plate. In a preferred embodiment, the first and second base plate displacing means each comprise a coaxial coarse-fine drive mechanism, and the instrument carrier vertical displacement means comprises a fine adjustment mechanism between the base plate and the stirrup.

Further objects, features and advantages of the present invention will become apparent from the detailed description of preferred embodiments which follows, when considered together with the attached figures of drawing.

BRIEF DESCRIPTION OF THE DRAWINGS

In the drawings:

FIG. 2 is a perspective overall view in a vertical arrangement; and

FIG. 3 is a schematic functional representation of isolated elements according to FIG. 1.

DETAILED DESCRIPTION OF PREFERRED EMBODIMENTS

Figure 1:
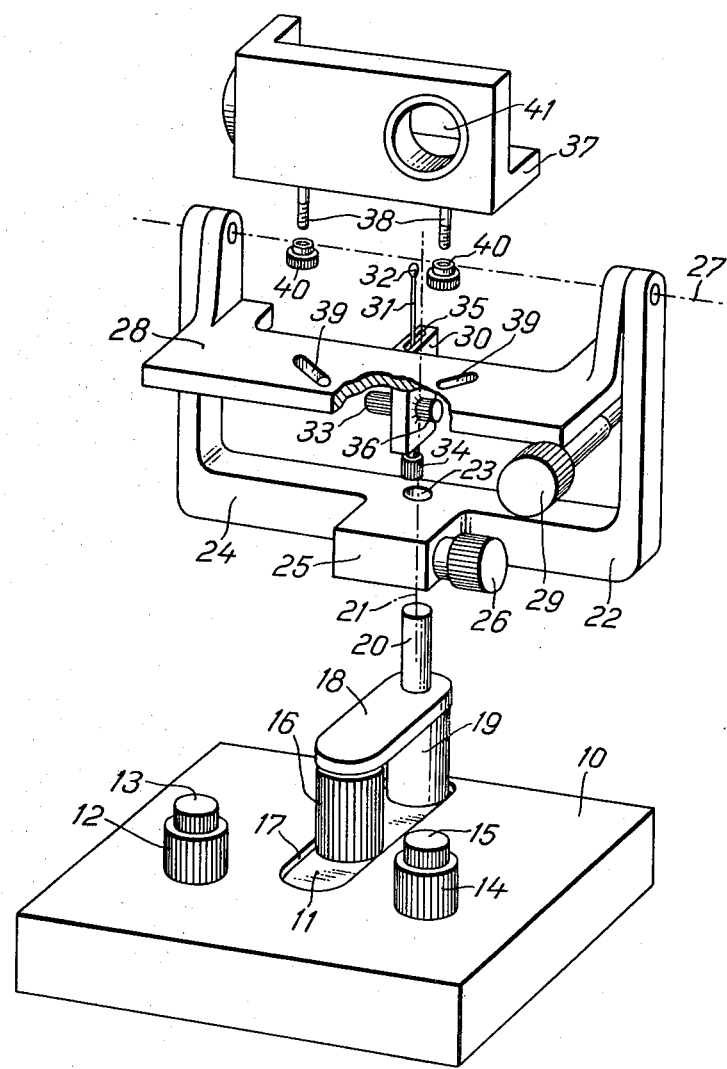
FIG. 1 is a perspective overall view of the instrument base in a horizontal arrangement.

In the instrument base according to the invention, between the base plate and the instrument carrier there is provided a stirrup rotatable around a vertical axis and a mounting plate rotatable around a horizontal axis and fastened to said stirrup for the instrument carrier which is displaceable on the mounting plate. There is also provided an adjustable carrier for an adjustable optical contact element, also mounted on the mounting plate, and the displacement of the base plate in the horizontal plane is effected in two coordinate directions by means of a coaxial coarse-fine drive in each. The adjustment in height of the instrument carrier is accomplished by means of a fine setting handle. The coarse-fine drives are arranged on the housing, and the fine setting handle is arranged on the base plate.

A particularly convenient and clearly observable mode of handling is achieved by locating the fine setting handle in a position offset with respect to the connecting line between the two coaxial coarse-fine drives and by providing a horizontally acting swivelling device on the stirrup.

It is of particular advantage to equip the mounting plate for its rotation with a drive actuated by means of a rotating knob and to provide the carrier for the optical contact element with means for its setting in at least one coordinate direction. All of the parts to be moved are thereby provided with setting means, whereby mistakes in the operation of the instrument are for the most part prevented, and the precise setting required for the contacting of the object may be effected without laborious searching for the adjusting means to be actuated.

On occasion it is unavoidable, primarily in stationary clinical areas, to perform examinations on patients in the prone position. For this purpose, it is of advantage to support the stirrup releasably on the vertical axis and to provide an angular intermediate piece, whereby the stirrup may be secured to the base plate after a rotation by 90°.

Advantageously, the instrument carrier is designed so that it has at least one holder for an optical observation instrument, for example, a microscope tube, an objective, an ocular lens or a photographic imaging device, and an illuminating device, for example, a lamp housing or a flash unit.

In the drawing, two exemplary embodiments of the instrument base according to the invention are illustrated schematically. Referring now to the drawings, FIGS. 1 and 2 illustrate an instrument base with an approximately square base plate 11, surrounded by a housing 10. For the purpose of horizontal displacement of the base plate 11 in two coordinate directions, a coaxial coarse-fine drive 12, 13 and 14, 15 for each adjustment is provided on the housing 10. These drives penetrate through the housing 10 and effect by means of known driving means, not shown, the displacement of the base plate 11. A fine adjusting handle 16 is arranged on the base plate 11 between the two coarse-fine drives 12, 13, and 14, 15. It is offset with respect to the connecting line of the two drives for better handling. It is not necessary to provide a coarse height adjusting device in this instance, because such an adjustment may be effected in a simple manner by means of the chin and forehead supports customarily mounted on the instrument base, with the dimensions of the body of the person performing the examination providing the initial indication for such an adjustment. While during a displacement of the instrument base in the X-direction the base plate 11 is moved together with the housing 10 over a support, not shown, for example, a table plate, only the base plate 11 is moved in the Y-direction when the coarse and fine drives 14, 15 are actuated, while the housing 10 remains fixedly on the support. For this reason, the housing 10 is equipped with an elongated hole 17, wherein the fine setting handle 16 is able to slide back and forth. The latter is connected drivingly on the side facing the base plate and is rigidly connected at its upper end by means of a cover plate 18 with an adjusting cylinder 19. A pivot 20 is formed onto the cover plate 18, with its vertical axis 21 coinciding with that of the adjusting cylinder 19. Upon actuation of the fine setting handle 16, the cover plate 18 is lifted together with the pivot 20.

A generally U-shaped stirrup 22 is removably mounted on the pivot 20, with the stirrup having in its horizontal bar 24 a recess 23 cylindrical in shape for receiving the pivot. A projection 25 is formed on the bar 24, and this is provided with a swivelling device 26 having a knurled knob for effecting horizontal rotation of the stirrup 22. At the upper end of the vertical arms of the stirrup, a support plate 28 rotatable around a horizontal axis 27 is mounted, while at the lower side of the support plate a rotating knob 29 for vertical rotation is arranged in the area of one of the arms of the stirrup, to cooperate drivingly with the arm. In the center of the support plate 28, on the side facing the examining person, a carrier 30 is provided for a contact element 31, the upper end of which in the present case carries a contact lens 32. The carrier 30 is capable of fine adjustment by means of knurled knobs 33, 34 acting on the corresponding drives. Adjustment is in the directions parallel and perpendicular to the support plate 28. The contact element 31 may be moved in an elongated slot 35 of the carrier 30. By means of an adjusting drive 36, the contact pressure on the object, for example, a human eye, may be controlled.

On the support plate 28, an angular instrument carrier 37 may be mounted by means of pins 38, integrally formed onto its underside. These pins are insertable into the slots 39 of the support plate 28. The fastening of the instrument carrier 37 to the support plate 28 is effected by way of pins 38 and slots 39 by means of clamping screws 40. The instrument carrier 37 is equipped with a holder 41, wherein optical observation instruments, such as microscope tubes, objectives, photographic imaging devices, together with illuminating devices, such as lamp housings of different types and dimensions, flash units, etc. may be interchangeably inserted.

The embodiment shown in FIG. 2 differs from that of FIG. 1 only in that the stirrup 22 and the support plate 28 may be secured to the base plate 28 after a rotation by 90°. To this extent, similar parts of the two embodiments are identified by identical reference symbols. The conversion of the stirrup 22 and of the support plate 28, together with the instrument carrier 37, not shown here, requires merely an intermediate angular piece 24, which on the one hand may be placed onto the pivot pin 20 of the cover plate 18 by means of a cylindrical bore 43, and on the other hand may be inserted with a pin 44 into the recess 23 of the stirrup 22, whereby a readily releasable connection is established. This vertical working position is provided for the examination of patients in the prone position, which is frequently required when the instrument base is used for intravital microscopy.

The mode of operation of the device according to the invention is explained hereinbelow with the aid of the functional representation of FIG. 3, wherein all of the parts not required for an understanding of the invention have been eliminated for the sake of clarity.

The coarse setting of the instrument base in the direction of the X-axis and the focusing in the direction of the Y-axis are effected by actuation of the coarse drives 12, 14, while the coarse setting in the direction of the Z-axis is effected by the height of the examining person when seated in combination with the adjustment of the forehead and chin supports, not shown. Following this coarse setting, fine adjustments in the direction of the X- and Y-axes are performed by means of the fine drives 13, 15, and in the direction of the Z-axis with the fine setting handle 16. A relatively large area of the object, for example, of an eye, may be examined by rotating the stirrup 22 around its vertical axis 21 in combination with a rotation of the support plate 28 around its horizontal axis 27. The stirrup 22 and the support plate 28 thereby describe horizontal or vertical circular arcs 45, 46, respectively, which intersect at a point representing the center of the optical observation assembly 47. The vertical axis 21 for the rotating motion of the stirrup 22 and the horizontal axis 27 for the rotating motion of the support plate 28 also intersect at a given point. In the case of eye examinations, this point represents the assumed center of curvature of the cornea of the eye to be examined. The knurled knobs 33, 34 serve for precision adjustment of the contact element 31 arranged on the carrier 30, and thus of the contact lens 32, in the direction of the X'- and Z'-coordinates designated by 48, 49. The setting of the contact element 31 in the direction of the Y'-coordinate 50, and thus the establishment of the contact pressure of the contact lens 32, is effected by means of the adjusting drive 36, which is connected by means of a spring 51 with the contact element 31.

To examine, for example, the endothelial structure of the rear side of the cornea, the instrument carrier 37 may be converted for oblique observation, so that the light is incident obliquely on the object plane and the observation is performed at the angle of reflection. For this purpose, it is sufficient to rotate the instrument carrier 37 in the slot 39 to the degree desired. It should be understood that the overall setting of the instrument base is maintained in the process.

What is claimed is:

1. An adjustable instrument base suitable for holding optical instruments, comprising:
    a base plate movable along first and second horizontal coordinate directions;
    a housing member surrounding said base plate, said housing member being movable with respect to said base plate in said first coordinate direction;
    first and second means mounted on said housing member for effecting displacement of said base plate in said first and second coordinate directions, respectively;
    a generally U-shaped stirrup member mounted on said base plate for rotation;
    a support plate mounted on said stirrup member for rotation about a horizontal axis;
    a first instrument carrier displaceably mounted on said support plate; and
    means mounted on said base plate for effecting vertical displacement of said first instrument carrier.

2. An instrument base as defined by claim 1, further comprising a second carrier for an optical contact element displaceably mounted on said support plate.

3. An instrument base as defined by claim 1, wherein said first and second base plate displacing means each comprise a coaxial coarse-fine drive mechanism, and said instrument carrier vertical displacement means comprises a fine adjustment mechanism between said base plate and said stirrup.

4. An instrument base as defined by claim 3, wherein said fine adjustment mechanism is offset in its position with respect to the line connecting said first and second coarse-fine drive mechanisms.

5. An instrument base as defined by claim 1, further comprising means on said stirrup for adjusting the horizontal rotation thereof.

6. An instrument base as defined by claim 1, further comprising means on said support plate for adjusting the vertical rotation thereof.

7. An instrument base as defined by claim 6, wherein said vertical rotation adjustment means on said support plate comprises a drive mechanism attached to said support plate and a rotatable knob for actuating said drive mechanism.

8. An instrument base as defined by claim 2, further comprising means on said second carrier for displacing the optical contact element in at least one coordinate direction.

9. An instrument base as defined by claim 1, further comprising means for mounting said stirrup on said base plate for rotation about a horizontal axis.

10. An instrument base as defined by claim 9, wherein said mounting means comprises an angular shaped intermediate piece.

11. An instrument base as defined by claim 1, wherein said instrument carrier comprises at least one support for an optical observation instrument and an illuminating device.

12. An instrument base as defined by claim 1, wherein said stirrup is rotatable about a vertical axis and wherein the vertical axis for rotation of the stirrup and the horizontal axis for rotation of the support plate intersect.

* * * * *